United States Patent [19]

Kropp et al.

[11] Patent Number: 4,909,985

[45] Date of Patent: Mar. 20, 1990

[54] TARNISH-RESISTANT PRECIOUS-METAL ALLOYS FOR DENTISTRY

[75] Inventors: Rudolf Kropp, Pforzheim; Wolfgang Küerten, Birkenfeld, both of Fed. Rep. of Germany

[73] Assignee: Degussa Aktiengesellschaft, Frankfurt, Fed. Rep. of Germany

[21] Appl. No.: 360,527

[22] Filed: Jun. 2, 1989

[30] Foreign Application Priority Data

Jun. 11, 1988 [DE] Fed. Rep. of Germany ....... 3819904

[51] Int. Cl.$^4$ ............................................. C22C 30/00
[52] U.S. Cl. .................................................... 420/587
[58] Field of Search ........................................ 420/587

[56] References Cited

U.S. PATENT DOCUMENTS 4,369,162  1/1983  Wagnet et al. ...................... 420/587

FOREIGN PATENT DOCUMENTS 61-67742  4/1986  Japan .
61-67743  4/1986  Japan .

Primary Examiner—L. Dewayne Rutledge
Assistant Examiner—David Schumaker
Attorney, Agent, or Firm—Beveridge, DeGrandi & Weilacher

[57] ABSTRACT

Economical, tarnish-resistant precious-metal alloys for dentistry consisting essentially of 36 to 39% silver, 28 to 32.5% gold, 17 to 19.5% palladium, 0 to 0.1% iridium, 9.5 to 10.5% copper, 0.5 to 3% indium and 0.5 to 2.5% zinc, whereby the sum of the indium and zinc contents does not exceed a maximum of 4%.

6 Claims, No Drawings

TARNISH-RESISTANT PRECIOUS-METAL ALLOYS FOR DENTISTRY

INTRODUCTION AND BACKGROUND

The present invention relates to tarnish-resistant precious-metal alloys based on silver, gold, palladium and copper with additives of indium and zinc for dentistry. The alloys of the present invention are especially well suited for casting crowns and bridges which are to be veneered with plastic or which remain unveneered.

Alloys with a content of at least 75% gold and platinum metals have proven to be superior in dentistry technology for decades but are quite expensive. Alloys with 50–60% gold and additives of 5–10% palladium have also been known for many years but are likewise relatively expensive.

Considerably less expensive precious-metal alloys are known; i.e. with a gold content below 50%, palladium content of 5–30%, with a high silver content and with additives o indium, copper and zinc. However, these alloys differ from the alloys with a higher gold content by virtue of the fact that they normally exhibit a two-phase structure.

This second phase is always heavily enriched with palladium an indium, which results in a depletion of these elements in the silver-rich matrix. However, the tarnish resistance of silver-rich alloys depends to a great extent on its palladium and indium content, both of which suppress the tarnishing of the surface by sulfides.

The two-phase feature of the structure of these prior known alloys is furthermore associated with the disadvantage that their corrosion potential can differ greatly vis-a-vis different anions and complexing agents, so that local element formations occur, which results in greater corrosion. Moreover, since the palladium-rich phase is harder than the silver-rich phase an uneven surface can readily occur during the polishing of a crown or bridge (orange skin).

A further disadvantage is the reduced deformability (elongation) of two-phase alloys.

SUMMARY OF THE INVENTION

An object of the present invention is to provide tarnish-resistant precious-metal alloys based on silver, gold, palladium and copper with additives of indium and zinc for dental technology. In particular, an object of the invention is to provide alloys for casting of crowns and bridges, which are economical, one-phase and corrosion-resistant and also exhibit a high degree of hardness and good deformability.

In achieving the above and other objects, a feature of the invention resides in tarnish-resistant precious-metal alloys consisting essentially of 36 to 39% by weight silver, 28 to 32.5% by weight gold, 17 to 19.5% by weight palladium, 0 to 0.1% by weight iridium, 9.5 to 10.5% by weight copper, 0.5 to 3% by weight indium and 0.5 to 2.5% by weight zinc, whereby the sum of indium and zinc does not exceed a maximum of 4% by weight.

The alloys of the present invention preferably contain 37 to 38% by weight silver, 30% by weight gold, 18 to 19% by weight palladium, 0 to 0.1% by weight iridium, 10% by weight copper, 1.5 to 2.5% by weight indium and 1 to 1.5% by weight zinc.

It was surprisingly found that there is a relatively narrow range of alloy compositions in the case of alloys based on silver, gold, palladium, copper, indium and zinc with approximately 30% gold which compositions exhibit both a high degree of hardness, permanent elongation limit and tensile strength. These advantageous properties are achieved even after a slow cooling-off of a casting in the casting mould. These alloys have a good plastic elongation as well. In addition, these alloys are single phase compositions and thus offer the desired prerequisite for a good resistance to tarnishing and corrosion. Alloys which meet these specified prerequisites have mass contents of 36–39% silver, 28–32.5% gold, 17–19.5% palladium, 0–0.1% iridium, 9.5 to 10.5% copper, 0.5–3.0 indium and 0.5–2.5% zinc, whereby the sum of indium and zinc does not exceed a maximum of 4%.

DETAILED EMBODIMENTS OF THE INVENTION

The following table indicates 13 alloys of which alloys 9–13 lie outside the composition of the invention and exhibit without exception a two-phase structure in which a phase rich in palladium, indium and zinc is embedded in a matrix phase rich in gold and silver. This latter matrix phase is baser in a corrosion-chemical sense vis-a-vis certain anions which occur in the saliva such as e.g. rhodanide and nitrite than the palladium-rich phase is and can therefore be preferentially attacked in the mouth. Alloys 10–12 are distinctly two-phase materials in spite of only slightly exceeding the composition of the invention and exhibit hardness values distinctly under 200 Hv (vickers pyramid hardness, diamond penetration hardness) after casting.

Alloys 1–8 are single phase after casting and attain hardness values of at least 230 Hv, 0.2% permanent elongation limits of at least 660 N/mm$^2$, tensile strengths of at least 795 N/mm$^2$ and rupture elongations of at least 10%. They are therefore distinctly superior to the known two-phase alloys.

Further variations and modifications of the present invention will be apparent to those skilled in the art and from the foregoing and are intended to be encompassed by the claims appended hereto.

German priority application P 38 19 904.1-42 is relied on and incorporated herein of reference.

TABLE

| Alloy No. | Composition in mass % | | | | | | | Melting Interval % | Number of Phases | Technical data, casting slowly cooled off | | | |
|---|---|---|---|---|---|---|---|---|---|---|---|---|---|
| | Au | Pd | Ir | Ag | Cu | In | Zn | | | HV hardness | Permanent Elongation limit | Tensile strength N/mm$^2$ | rupture elongation % |
| 1 | 29.0 | 18.9 | 0.1 | 38.0 | 10.0 | 2.5 | 1.5 | 1015–905 | 1 | 245 | 730 | 850 | 13 |
| 2 | 31.0 | 18.9 | 0.1 | 36.5 | 10.0 | 2.5 | 1.0 | 1020–930 | 1 | 255 | 810 | 910 | 11 |
| 3 | 28.0 | 19.4 | 0.1 | 38.5 | 10.5 | 2.0 | 1.5 | 1020–930 | 1 | 230 | 720 | 835 | 12 |
| 4 | 30.0 | 18.9 | 0.1 | 38.0 | 10.0 | 2.0 | 1.0 | 1030–935 | 1 | 260 | 775 | 880 | 12 |
| 5 | 30.0 | 18.9 | 0.1 | 37.5 | 10.0 | 2.0 | 1.5 | 1015–925 | 1 | 255 | 725 | 845 | 10 |
| 6 | 30.0 | 18.9 | 0.1 | 37.5 | 10.0 | 2.5 | 1.0 | 1025–920 | 1 | 260 | 765 | 861 | 12 |
| 7 | 30.0 | 18.9 | 0.1 | 38.0 | 10.0 | 1.5 | 1.5 | 1020–935 | 1 | 255 | 725 | 855 | 15 |
| 8 | 32.0 | 17.5 | — | 37.0 | 9.5 | 1.5 | 2.5 | 995–910 | 1 | 230 | 660 | 795 | 10 |

TABLE-continued

| Alloy No. | Composition in mass % | | | | | | | Melting Interval % | Number of Phases | Technical data, casting slowly cooled off | | | |
|---|---|---|---|---|---|---|---|---|---|---|---|---|---|
| | Au | Pd | Ir | Ag | Cu | In | Zn | | | HV hardness | Permanent Elongation limit | Tensile strength N/mm$^2$ | rupture elongation % |
| 9 | 20.0 | 21.0 | 0.1 | 39.0 | — | 16.0 | 4.0 | 1035–860 | 2 | 155 | 280 | 565 | 8 |
| 10 | 28.0 | 17.9 | 0.1 | 40.5 | 9.5 | 0.5 | 3.5 | 985–890 | 2 | 160 | | | |
| 11 | 30.0 | 17.9 | 0.1 | 39.0 | 9.5 | 0.5 | 3.0 | 990–900 | 2 | 170 | | | |
| 12 | 32.5 | 17.0 | 0.1 | 37.0 | 9.5 | 1.0 | 3.0 | 980–920 | 2 | 185 | | | |
| 13 | 40.0 | 7.9 | 0.1 | 35.0 | 7.0 | 5.0 | 3.5 | 850–770 | 2 | 245 | 650 | 780 | 7 |

We claim:

1. A tarnish-resistant precious-metal alloy based on silver, gold, palladium and copper with additives of indium and zinc for dentistry, consisting essentially of 36 to 39% by weight silver, 28 to 32.5% by weight gold, 17 to 19.5% by weight palladium, 0 to 0.1% by weight iridium, 9.5 to 10.5% by weight copper, 0.5 to 3% by weight indium and 0.5 to 2.5% by weight zinc, whereby the sum of indium and zinc does not exceed a maximum of 4% by weight.

2. The tarnish-resistant precious-metal alloy according to claim 1, consisting essentially of 37 to 38% by weight silver, 30% by weight gold, 18 to 19% by weight palladium, 0 to 0.1% by weight iridium, 10% by weight copper, 1.5 to 2.5% by weight indium and 1.0 to 1.5% by weight zinc.

3. A dental crown made from the tarnish-resistant metal alloy defined by claim 1.

4. A dental bridge made from the tarnish-resistant metal alloy defined by claim 1.

5. A dental crown made from the tarnish-resistant metal alloy defined in claim 2.

6. A dental bridge made from the tarnish-resistant metal alloy defined in claim 2.

* * * * *